US010485232B2

(12) United States Patent
Wright et al.

(10) Patent No.: US 10,485,232 B2
(45) Date of Patent: *Nov. 26, 2019

(54) AUXIN HERBICIDAL MIXTURES

(71) Applicant: Monsanto Technology LLC, St. Louis, MO (US)

(72) Inventors: Daniel R. Wright, St. Louis, MO (US); Junhua Zhang, Chesterfield, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/654,883

(22) Filed: Jul. 20, 2017

(65) Prior Publication Data
US 2018/0007896 A1    Jan. 11, 2018

Related U.S. Application Data

(63) Continuation of application No. 14/440,511, filed as application No. PCT/US2013/068411 on Nov. 5, 2013, now Pat. No. 9,743,662.

(60) Provisional application No. 61/722,440, filed on Nov. 5, 2012.

(51) Int. Cl.
| | |
|---|---|
| A01N 33/12 | (2006.01) |
| A01N 25/00 | (2006.01) |
| A01N 57/20 | (2006.01) |
| A01N 37/40 | (2006.01) |
| A01N 39/04 | (2006.01) |
| A01N 43/36 | (2006.01) |
| A01N 43/40 | (2006.01) |
| A01N 43/50 | (2006.01) |

(52) U.S. Cl.
CPC ............. *A01N 33/12* (2013.01); *A01N 25/00* (2013.01); *A01N 37/40* (2013.01); *A01N 39/04* (2013.01); *A01N 43/36* (2013.01); *A01N 43/40* (2013.01); *A01N 43/50* (2013.01); *A01N 57/20* (2013.01)

(58) Field of Classification Search
CPC .... A01N 2300/00; A01N 43/40; A01N 37/40; A01N 33/12
See application file for complete search history.

(56) References Cited

U.S. PATENT DOCUMENTS

| | | | |
|---|---|---|---|
| 2,505,059 | A | 4/1950 | Moore |
| 3,013,054 | A | 12/1961 | Richter |
| 3,276,856 | A | 10/1966 | Esposito et al. |
| 3,600,407 | A | 8/1971 | Levin et al. |
| 3,852,340 | A | 12/1974 | Reck et al. |
| 3,870,732 | A | 3/1975 | Hokama |
| 3,910,974 | A | 10/1975 | Hokama |
| 3,923,849 | A | 12/1975 | Hokama |
| 4,546,196 | A | 10/1985 | Luteri et al. |
| 4,729,781 | A | 3/1988 | Williams |
| 5,175,353 | A | 12/1992 | Jones et al. |
| 5,266,553 | A | 11/1993 | Champion et al. |
| 5,710,103 | A | 1/1998 | Magin et al. |
| 6,300,323 | B1 | 10/2001 | Haga et al. |
| 6,410,783 | B1 | 6/2002 | Peterson et al. |
| 6,881,707 | B2 | 4/2005 | Howat et al. |
| 8,232,265 | B2 | 7/2012 | Rogers et al. |
| 8,802,596 | B2 | 8/2014 | Rogers et al. |
| 9,049,866 | B2 | 6/2015 | Refardt et al. |
| 9,743,662 | B2 * | 8/2017 | Zhang ..................... A01N 25/00 |
| 2002/0107149 | A1 | 8/2002 | Volgas et al. |
| 2005/0026780 | A1 | 2/2005 | Parrish |
| 2007/0082819 | A1 | 4/2007 | Perry et al. |
| 2007/0093462 | A1 | 4/2007 | Rogers et al. |
| 2007/0184980 | A1 | 8/2007 | Roberts et al. |
| 2008/0207452 | A1 | 8/2008 | Kramer et al. |
| 2008/0207453 | A1 | 8/2008 | Kramer et al. |
| 2010/0173943 | A1 | 7/2010 | Jeschke et al. |
| 2011/0034332 | A1 | 2/2011 | Becher et al. |
| 2012/0142532 | A1 * | 6/2012 | Wright ................... A01N 25/32 |
| | | | 504/144 |
| 2012/0184434 | A1 | 7/2012 | Xu et al. |
| 2013/0109572 | A1 | 5/2013 | Pernak et al. |

FOREIGN PATENT DOCUMENTS

| | | |
|---|---|---|
| CA | 1293974 C | 1/1992 |
| DE | 4030687 A1 | 5/1991 |
| EP | D375624 A1 | 6/1990 |
| EP | 2305032 A1 | 4/2011 |
| GB | 851008 A | 10/1960 |
| RU | 2208930 C1 | 7/2003 |
| RU | 2366176 C2 | 9/2009 |
| RU | 2384064 C1 | 3/2010 |

(Continued)

OTHER PUBLICATIONS

Behrens, et al., "Dicamba Volatility," 1979, Weed Source, 27/5:486-493.
D'Sa, et al., "4,5-Dimethylimidazole: A Correction and Alternative Synthesis," 1991, J Heterocyclic Chem, 28, 1819-1920, XP055055998.
Duff, et al., "Identification of Carboxylic Acids: Use of N-Methylpiperazine and N-Phenylpiperazine," 1969, J Chem Ed, ACS, 46:388-390, XP009141119.

(Continued)

*Primary Examiner* — Johann R Richter
*Assistant Examiner* — Danielle Sullivan
(74) *Attorney, Agent, or Firm* — Stinson LLP; Erin C. Robert

(57) ABSTRACT

Herbicidal mixtures comprising an auxin herbicide and an adjuvant comprising a salt having a quaternary ammonium cation and/or a phosphonium cation are described. The adjuvant reduces the volatility of the auxin herbicide and/or counteracts the negative impact on the volatility of the auxin herbicide caused by the addition of a co-herbicide. Methods of preparing the herbicidal mixtures are also described.

27 Claims, No Drawings

(56) References Cited

FOREIGN PATENT DOCUMENTS

| RU | 2408188 C1 | 1/2011 |
|---|---|---|
| WO | 2003024218 A1 | 3/2003 |
| WO | 2005087007 A1 | 9/2005 |
| WO | 2008106107 A1 | 9/2008 |
| WO | 2008106118 A2 | 9/2008 |
| WO | 2008148483 A1 | 12/2008 |
| WO | 2010071936 A1 | 7/2010 |
| WO | 2010102102 A1 | 9/2010 |
| WO | 2010147966 A1 | 9/2010 |
| WO | 2011019652 A2 | 2/2011 |
| WO | 2011026800 A2 | 3/2011 |
| WO | 2011039172 A2 | 4/2011 |
| WO | 2012006313 A2 | 1/2012 |
| WO | 2012059494 A1 | 5/2012 |
| WO | 2013017402 A1 | 2/2013 |
| WO | 2013063357 A3 | 5/2013 |
| WO | 2013184622 A3 | 12/2013 |
| ZA | 8907205 | 6/1990 |

OTHER PUBLICATIONS

Giesemann, et al., "Untersuhungen über 1-Triphenylmethyl-imidazole, I," 1959, Chemische Berichte, 92:92-96, XP055056003.
Hatzios, et al., "Pelargonic Acid," 1998, WAASA Herbicide handbook, pp. 55-57, 3 pages, XP002953604.
Pernak, et al., "Ionic Liquids with Herbicidal Anions," 2011, Tetrahedron, 67:4838-4844, XP028227648.
Pernak, et al., "2,4-D Based Herbicidal Ionic Liquids," 2012, Tetrahedron, 68:4267-4273, XP028479458.
Prigot et al., "Derivatives of Piperazine. XXII. Piperazinium Salts for Utilization in Identification of Organic Acids," 1948, J Am Chem Soc, 70:2758-2759, XP055056011.
Bredereck, H., et al., "Imidazolsynthesen mit Formamid (Formamid-Reaktionen, I. Mitteil.)," 1953, Chemische Berichte, 86:88-95, XP055056002.
English Abstract Only RU2395203, 1 page.
International Search Report dated Mar. 3, 2014, in International PCT Application No. PCT/US2013/068411, 4 pages.
Written Opinion dated Mar. 3, 2014, in International PCT Application No. PCT/US2013/068411, 6 pages.

* cited by examiner

AUXIN HERBICIDAL MIXTURES

REFERENCE TO RELATED APPLICATIONS

This application is a continuation of U.S. application Ser. No. 14/440,511, filed May 4, 2015, which is a U.S. National Stage Application based on International Application Serial No. PCT/US2013/068411, filed Nov. 5, 2013, which claims the benefit of U.S. Provisional Application Ser. No. 61/722,440, filed Nov. 5, 2012, the entire contents of each of which are incorporated herein by reference.

FIELD OF THE INVENTION

The present invention relates to herbicidal mixtures comprising an auxin herbicide and an adjuvant comprising a salt having a quaternary ammonium cation and/or a phosphonium cation. The adjuvant reduces the volatility of the auxin herbicide and/or counteracts the negative impact on the volatility of the auxin herbicide caused by the addition of a co-herbicide.

BACKGROUND OF THE INVENTION

Auxin herbicides have proven to be effective and highly beneficial for control of unwanted plants. Auxin herbicides include 3,6-dichloro-2-methoxybenzoic acid (dicamba); 2,4-dichlorophenoxyacetic (2,4-D); 4-(2,4-dichlorophenoxy)butanoic acid (2,4-DB); 2-(2,4-dichlorophenoxy)propanoic acid (dichloroprop); 2-(4-chloro-2-methylphenoxy) acetic acid (MCPA); 4-(4-chloro-2-methylphenoxy)butanoic acid (MCPB); 4-amino-3,6-dichloro-2-pyridinecarboxylic acid (aminopyralid); 3,6-dichloro-2-pyridinecarboxylic acid (clopyralid); 2-[(4-amino-3,5-dichloro-6-fluoro-2-pyridinyl)oxy]acetic acid (fluroxypyr); [(3,5,6-trichloro-2-pyridinyl)oxy]acetic acid (triclopyr); 2-(4-chloro-2-methylphenoxy)propanoic acid (mecoprop); 4-amino-3,5,6-trichloro-2-pyridinecarboxylic acid (picloram); 3,7-dichloro-8-quinolinecarboxylic acid (quinclorac); 6-amino-5-chloro-2-cyclopropyl-4-pyrimidinecarboxylic acid (aminocyclopyrachlor); agriculturally acceptable salts or other derivatives of any of these herbicides; racemic mixtures and resolved isomers thereof; and mixtures thereof. Generally, auxin herbicides mimic or act like natural auxin plant growth regulators. Auxin herbicides appear to affect cell wall plasticity and nucleic acid metabolism, which can lead to uncontrolled cell division and growth. The injury symptoms caused by auxin herbicides include epinastic bending and twisting of stems and petioles, leaf cupping and curling, and abnormal leaf shape and venation.

Off-site movement is sometimes associated with auxin herbicides. Under some application conditions, auxin herbicides can volatilize into the atmosphere and migrate from the application site to adjacent crop plants or non-target plants where contact damage can occur. Typical symptoms of injury to crop plants include leaf cupping, leaf malformation, leaf necrosis, terminal bud kill and/or delayed maturity.

Accordingly, there remains a need for an economic, convenient solution that reduces volatility of auxin herbicides. A solution that does not require costly modifications to existing herbicide production or formulation processes would be beneficial. Furthermore, a solution that can be used with conventional auxin herbicide formulations and that can be practiced in field during preparation of auxin herbicide-containing herbicide mixtures (e.g., tank mixes) would be advantageous.

Further, with the development of transgenic crop plants including stacked traits, such as dicamba tolerance, 2,4-D tolerance, and glyphosate tolerance traits, herbicidal mixtures containing an auxin herbicide and a co-herbicide are particularly beneficial and convenient for control of unwanted plants. However, addition of a co-herbicide to auxin herbicidal mixtures has been known to affect the volatility of the auxin herbicide and increase off-site movement of the herbicide. For example, tank mixing of auxin herbicides such as dicamba or 2,4-D with certain co-herbicides, such as glyphosate, has been known to exacerbate problems associated with volatility of the auxin herbicide. Accordingly, there remains a need for an economic, convenient solution that reduces or controls the negative effects on auxin volatility resulting from the addition of a co-herbicide.

As will be clear from the disclosure that follows, these and other benefits are provided by the present invention.

SUMMARY OF THE INVENTION

The present invention provides for methods of preparing a herbicidal mixture. In one aspect, the method comprises combining an auxin herbicide comprising a first cation and an adjuvant comprising a salt having a second cation, wherein the salt is selected from the group consisting of:

(a) an ammonium salt of Formula I

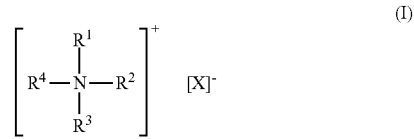

wherein $R^1$, $R^2$, $R^3$, and $R^4$ are independently a $C_1$-$C_{12}$ hydrocarbyl and X is an agronomically acceptable anion;

(b) a salt containing a nitrogen heterocycle of Formula II

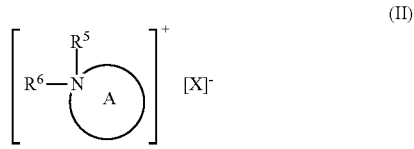

wherein A is a 5 or 6-membered heterocyclic ring; $R^5$ is a $C_1$-$C_{20}$ alkyl; $R^6$ is hydrogen or a $C_1$-$C_6$ alkyl, and X is an agronomically acceptable anion;

(c) a phosphonium salt of Formula III

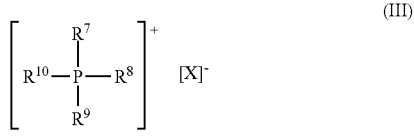

wherein $R^7$, $R^8$, $R^9$, and $R^{10}$ are independently a $C_1$-$C_{12}$ hydrocarbyl and X is an agronomically acceptable anion; and mixtures thereof, wherein the herbicidal mixture has a total herbicide concentration no greater than about 40% by weight acid equivalent (a.e).

The present invention is also directed to various herbicidal mixtures prepared in accordance with these methods, various adjuvant compositions, and application methods using the herbicidal mixtures.

Other objects and features will be in part apparent and in part pointed out hereinafter.

DESCRIPTION OF THE PREFERRED EMBODIMENTS

In general, the present invention relates to herbicidal mixtures and methods that provide for reduced auxin herbicide volatility following application of the auxin herbicide to the foliage of target plants. The herbicidal mixtures of the present invention include concentrate compositions and application mixtures (e.g., tank mixes or ready-to-use formulations) comprising an auxin herbicide and an adjuvant. When mixed with the auxin herbicide, the adjuvant reduces the volatility of the auxin herbicide and/or counteracts the negative impact on the volatility of the auxin herbicide caused by addition of an optional co-herbicide. Advantageously, the adjuvant can be used with existing stocks of conventional auxin herbicides. Thus, the present invention provides herbicidal mixtures and preparation methods that are convenient and effective for controlling the volatility of auxin herbicides.

In accordance with the present invention, the herbicidal mixtures comprise an auxin herbicide comprising a first cation (i.e., at least a portion of the auxin herbicide is not in free acid form) and an adjuvant comprising a salt having a second cation. The herbicidal mixtures are prepared by a method comprising combining an auxin herbicide and adjuvant in a liquid medium (e.g., water).

Suitable auxin herbicides include, for example, 3,6-dichloro-2-methoxybenzoic acid (dicamba); 2,4-dichlorophenoxyacetic (2,4-D); 4-(2,4-dichlorophenoxy)butanoic acid (2,4-DB); 2-(2,4-dichlorophenoxy)propanoic acid (dichloroprop); 2-(4-chloro-2-methylphenoxy)acetic acid (MCPA); 4-(4-chloro-2-methylphenoxy)butanoic acid (MCPB); 4-amino-3,6-dichloro-2-pyridinecarboxylic acid (aminopyralid); 3,6-dichloro-2-pyridinecarboxylic acid (clopyralid); 2-[(4-amino-3,5-dichloro-6-fluoro-2-pyridinyl)oxy]acetic acid (fluroxypyr); [(3,5,6-trichloro-2-pyridinyl)oxy]acetic acid (triclopyr); 2-(4-chloro-2-methylphenoxy)propanoic acid (mecoprop); 4-amino-3,5,6-trichloro-2-pyridinecarboxylic acid (picloram); 3,7-dichloro-8-quinolinecarboxylic acid (quinclorac); 6-amino-5-chloro-2-cyclopropyl-4-pyrimidinecarboxylic acid (aminocyclopyrachlor); agriculturally acceptable salts or other derivatives of any of these herbicides; racemic mixtures and resolved isomers thereof; and mixtures thereof. In particular, dicamba and 2,4-D have proven to be effective auxin herbicides. Accordingly, in various embodiments, the auxin herbicide is selected from the group consisting of dicamba, 2,4-D, and salts thereof.

In certain embodiments, the auxin herbicide comprises one or more salts of 2,4-D. Salts of 2,4-D include, for example, the alkali salts and organic ammonium salts, which are commonly referred to as amine salts. Accordingly, salts of 2,4-D include the sodium, potassium, monoethanolamine, diethanolamine, triethanolamine, tri-isopropanol amine and N,N,N-trimethylethanolamine (choline), isopropylamine, dimethylamine, and trimethylamine salts. Some preferred 2,4-D salts are selected from the group consisting of the dimethylamine salt, choline salt, and mixtures thereof.

In various embodiments, the auxin herbicide comprises dicamba and more particularly one or more salts of dicamba. Typical salts of dicamba are, for example, the alkali salts and organic ammonium salts, which are commonly referred to as amine salts. These salts include the sodium, potassium, monoethanolamine, diethanolamine, isopropylamine, diglycolamine, dimethylamine salts and mixtures thereof. Some preferred dicamba salts are selected from the group consisting of the diglycolamine salt, potassium salt, and mixtures thereof. In certain embodiments, the auxin herbicide comprises the monoethanolamine salt or potassium salt of dicamba. In other embodiments, the auxin herbicide comprises the diglycolamine salt of dicamba.

Other salts of dicamba for use in the practice of the present invention include polyamine salts such as those described in United States Patent Application Publication 2012/0184434, the entire disclosure of which is incorporated herein by reference for all relevant purposes. The salts described in US 2012/0184434 include an anionic pesticide, such as dicamba, and a cationic polyamine of formula (A)

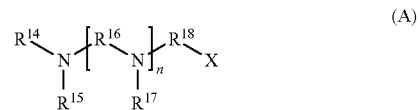

wherein $R^{14}$, $R^{15}$, $R^{17}$, $R^{19}$ and $R^{20}$ are independently H or $C_1$-$C_6$-alkyl, which is optionally substituted with OH, $R^{16}$ and $R^{18}$ are independently $C_2$-$C_4$-alkylene, X is OH or $NR^{19}R^{20}$, and n is from 1 to 20; or a cationic polyamine of formula (B)

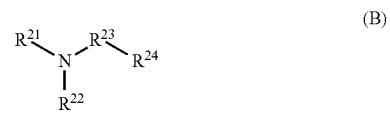

wherein $R^{21}$ and $R^{22}$ are independently H or $C_1$-$C_6$-alkyl, $R^{23}$ is $C_1$-$C_{12}$-alkylene, and $R^{24}$ is an aliphatic $C_5$-$C_8$ ring system, which comprises either nitrogen in the ring or which is substituted with at least one unit $NR^{21}R^{22}$. Examples of these cationic polyamines include tetraethylenepentamine, triethylenetetramine, diethylenetriamine, pentamethyldiethylenetriamine, N,N,N',N'',N''-pentamethyl-dipropylenetriamine, N,N-bis(3-dimethylaminopropyl)-N-isopropanolamine, N'-(3-(dimethylamino)propyl)-N,N-dimethyl-1,3-propanediamine, N,N-bis(3-aminopropyl)methylamine, N-(3-dimethylaminopropyl)-N,N-diisopropanolamine, N,N,N'-trimethylaminoethyl-ethanolamine, aminopropylmonomethylethanolamine, and aminoethylethanolamine. Accordingly, in various embodiments, the auxin herbicide comprises a dicamba salt comprising a cationic polyamine of formula A or B above.

In various embodiments, the herbicidal mixture further comprises a co-herbicide. Co-herbicides include, for example, acetyl CoA carboxylase (ACCase) inhibitors; acetolactate synthase (ALS) or acetohydroxy acid synthase (AHAS) inhibitors; photosystem II inhibitors; photosystem I inhibitors; protoporphyrinogen oxidase (PPO or Protox) inhibitors; carotenoid biosynthesis inhibitors; enolpyruvyl shikimate-3-phosphate (EPSP) synthase inhibitor; glutamine synthetase inhibitor; dihydropteroate synthetase inhibitor; mitosis inhibitors; 4-hydroxyphenyl-pyruvate-dioxygenase (4-HPPD) inhibitors; auxin transport inhibitors; nucleic acid inhibitors; agriculturally acceptable salts, esters and other derivatives of these herbicides; racemic mixtures and resolved isomers thereof; and combinations thereof. Specific examples of suitable co-herbicides include acetochlor; acifluorfen; alachlor; atrazine; azafenidin; bifenox; butachlor; butafenacil; carfentrazone-ethyl; diuron; dithiopyr; flufenpyr-ethyl; flumiclorac-pentyl; flumioxazin; fluoroglycofen; fluthiacet-methyl; fomesafen, N-(phosphonomethyl)glycine (glyphosate); DL-phosphinothricin (glufosinate); imazethapyr; lactofen; metazochlor; metolachlor (and S-metolachlor); metribuzin; oxadiargyl; oxadiazon; oxyfluorfen; pretilachlor; propachlor; propisochlor; pyraflufen-ethyl; sulfentrazone; thenylchlor; and agriculturally salts, esters and other derivatives thereof racemic mixtures and resolved isomers thereof, and combinations thereof. In some embodiments, the co-herbicide is a photosystem II inhibitor selected from, for example, ametryn, amicarbazone, atrazine, bentazon, bromacil, bromoxynil, chlorotoluron, cyanazine, desmedipham, desmetryn, dimefuron, diuron, fluometuron, hexazinone, ioxynil, isoproturon, linuron, metamitron, methibenzuron, metoxuron, metribuzin, monolinuron, phenmedipham, prometon, prometryn, propanil, pyrazon, pyridate, siduron, simazine, simetryn, tebuthiuron, terbacil, terbumeton, terbuthylazine and trietazine, salts and esters thereof, and mixtures thereof. In another embodiment, the co-herbicide is a 4-HPPD inhibitor selected from, for example, mesotrione, isoxaflutole, benzofenap, pyrazolynate, pyrazoxyfen, sulcotrione, tembotrione, and tropramezone.

In accordance with some embodiments, the co-herbicide is a graminicide selected from butroxydim, clethodim, cycloxydim, sethoxydim, tepraloxydim, tralkoxydim, profoxydim, haloxyfop, propaquizafop and the $C_{1-4}$ alkyl and propargyl esters of clodinafop, cyhalofop, diclofop, fenoxaprop, fluazifop, fluazifop-P, haloxyfop, quizalofop and quizalofop-P (e.g., quizalofop-ethyl or quizalofop-P-ethyl, clodinafop-propargyl, cyhalofop-butyl, diclofop-methyl, fenoxaprop-P-ethyl, fluazifop-P-butyl, haloxyfop-methyl, haloxyfop-R-methyl).

Some preferred co-herbicides include, for example, N-(phosphonomethyl)glycine (glyphosate); DL-phosphinothricin (glufosinate); atrazine; acetochlor; fomesafen; flumioxazin; lactofen; sulfentrazone; metribuzin; clethodim; sethoxydim; metolachlor; alachlor; fenoxaprop; fluazifop; haloxyfop-methyl; paraquat; trialkoxydim; agriculturally acceptable salts or other derivatives of any of these herbicides; and mixtures thereof.

It has been observed that the volatility of some auxin herbicides increases when mixed with a co-herbicide, particularly a co-herbicide that is more acidic in solution (i.e., has the potential to donate a free proton) than the auxin herbicide. For example, co-herbicides with a pKa or first pKa that is less than about 5 have been observed to increase the volatility of some auxin formulations (e.g., dicamba) when mixed. Co-herbicides that have a first pKa less than about 5 include, for example, glyphosate and glufosinate. Nevertheless, herbicidal mixtures containing auxin herbicides and these co-herbicides are desired because of their effectiveness and the development of transgenic crops that are tolerant to both auxin herbicides and certain co-herbicides. Accordingly, in various preferred embodiments, the co-herbicide is selected from the group consisting of glyphosate, glufosinate, agriculturally acceptable salts, esters or other derivatives thereof and mixtures thereof.

In some embodiments, the co-herbicide comprises one or salts of glyphosate. Glyphosate salts include mono, di- or tribasic and include ammonium (e.g., mono-, di- or triammonium), alkali metal (e.g., potassium or sodium), sulfonium (e.g., mono-, di- or trimethylsulfonium) and organic ammonium salts of glyphosate. The organic ammonium salts, commonly referred to as amine salts, can comprise aliphatic or aromatic amine salts and can include primary, secondary, tertiary or quaternary amine salts. Representative examples of such organic amine salts include isopropylamine, n-propylamine, ethylamine, dimethylamine, monoethanolamine, ethylenediamine and hexamethylenediamine salts of glyphosate. Representative examples of such organic amine salts include isopropylamine, n-propylamine, ethylamine, dimethylamine, monoethanolamine, ethylenediamine and hexamethylenediamine salts of glyphosate. Accordingly, in various embodiments, the glyphosate salt is selected from the group consisting of the potassium salt, monoammonium salt, diammonium salt, sodium salt, monoethanolamine salt, n-propylamine salt, isopropylamine salt, ethylamine salt, dimethylamine salt, ethylenediamine salt, hexamethylenediamine salt, trimethylsulfonium salt and mixtures thereof (e.g., the potassium salt, monoethanolamine salt, isopropylamine salt, and mixtures thereof). The alkali salts of glyphosate have been found to be particularly suitable for achieving high herbicidal loadings in glyphosate concentrate compositions. Thus, in some embodiments, the co-herbicide comprises a glyphosate salt comprising an alkali salt (e.g., the potassium and/or sodium salt). In some embodiments, the co-herbicide comprises glyphosate in the form of the potassium salt.

In general, the total herbicide content (auxin herbicide and co-herbicide) of the herbicidal mixture is no greater than about 40 by weight acid equivalent (a.e.). The term "acid equivalent" or "a.e." has a standard and well-known definition to those skilled in the art. The term refers to the theoretical amount of herbicide acid present (which has been formulated as a derivative) without taking into account the weight of the counter-ion present (e.g., the salt or ester counter-ion). In some embodiments, the herbicidal mixture is a concentrate composition wherein the total herbicide content is from about 10 wt. % a.e. to about 40 wt. % a.e., from about 15 wt. % a.e. to about 40 wt. % a.e., or from about 20 wt. % a.e. to about 40 wt. % a.e. In other embodiments, the herbicidal mixture is an application mixture (e.g., tank mix or ready-to-use formulation) wherein the total herbicide content is less than about 10 wt. % a.e. (e.g., from about 0.1 wt. % a.e. to about 10 wt. % a.e., from about 0.1 wt. % a.e. to about 8 wt. % a.e., from about 0.1 wt. % a.e. to about 5 wt. % a.e.). As understood by those skilled in the art, the total herbicide concentration of the application mixture may be adjusted with dilution water depending upon various factors such as the type of unwanted plants to be controlled and herbicide application rate.

When a co-herbicide is present, the herbicidal mixtures generally include relatively equal proportions or an excess of the co-herbicide to the auxin herbicide on an acid equivalent basis. In various embodiments, the acid equivalent weight ratio of co-herbicide to auxin herbicide ranges from about 1:1 to about 5:1, from about 1:1 to about 3:1, from about 1.5:1 to about 3:1, from about 1.5:1 to about 2.5:1, or from about 1.5:1 to about 2:1. In certain embodiments, the acid equivalent weight ratio of co-herbicide to auxin herbicide is about 1.5:1, about 2:1, or about 3:1.

In embodiments where the herbicidal mixture is an application mixture, the concentration of the auxin herbicide is typically from about 0.25 wt. % a.e. to about 6 wt. % a.e., from about 0.25 wt. % a.e. to about 4 wt. % a.e., or from about 0.5 wt. % a.e. to about 2 wt. % a.e. Also, in these embodiments, the concentration of the optional co-herbicide is typically from about 0.5 wt. % a.e. to about 8 wt. % a.e., from about 1 wt. % a.e. to about 6 wt. % a.e., or from about 1 wt. % a.e. to about 4 wt. % a.e.

In accordance with the present invention, the herbicidal mixture comprises an adjuvant used to reduce or control auxin herbicide volatility. The adjuvant comprises a salt selected from the group consisting of:

(a) an ammonium salt of Formula I

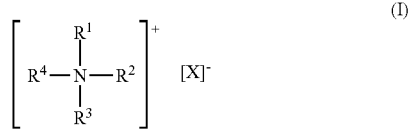

wherein $R^1$, $R^2$, $R^3$, and $R^4$ are independently a $C_1$-$C_{12}$ hydrocarbyl and X is an agronomically acceptable anion;

(b) a salt containing a nitrogen heterocycle of Formula II

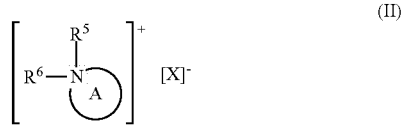

wherein A is a 5 or 6-membered heterocyclic ring; $R^5$ is a $C_1$-$C_{20}$ alkyl; $R^6$ is hydrogen or a $C_1$-$C_6$ alkyl, and X is an agronomically acceptable anion;

(c) a phosphonium salt of Formula III

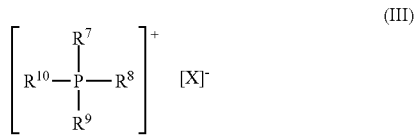

wherein $R^7$, $R^8$, $R^9$, and $R^{10}$ are independently a $C_1$-$C_{12}$ hydrocarbyl and X is an agronomically acceptable anion; and mixtures thereof. The term "hydrocarbyl" as used herein describes organic moieties consisting exclusively of the elements carbon and hydrogen and preferably containing 1 to about 50 carbon atoms, preferably 1 to about 30 carbon atoms, and even more preferably 1 to about 20 carbon atoms, including branched or unbranched, saturated or unsaturated and cyclic species. These moieties include alkyl, alkenyl, alkynyl, and aryl moieties optionally substituted with other aliphatic or cyclic hydrocarbon groups, such as alkaryl, alkenaryl and alkynaryl.

In various embodiments, $R^1$, $R^2$, $R^3$, and $R^4$ of the ammonium salt of Formula I are independently $C_1$-$C_{12}$ alkyl or benzyl. In some embodiments, $R^1$, $R^2$, $R^3$, and $R^4$ are independently $C_1$-$C_6$ alkyl. In preferred embodiments, the ammonium salt of Formula I is selected from the group consisting of tetraethylammonium chloride, tributylmethylammonium chloride, tetrabutylammonium chloride, tetrabutylammonium bromide, and dodecyltrimethylammonium chloride.

In various embodiments, ring A of the salt of Formula II is a substituted imidazole ring, a substituted pyridine ring, or a substituted pyrrolidine ring. Also, in these and other embodiments, $R^5$ is $C_1$-$C_{12}$ alkyl. In preferred embodiments, the salt of Formula II is selected from the group consisting of 1-butyl-1-methyl-pyrrolidinium chloride, 1-ethyl-3-methylimidazolium chloride, 1-butyl-3-methylimidazolium chloride, 1-methyl-3-octylimidazolium chloride, cetylpyridinium chloride, and cetylpyridinium bromide.

In various embodiments, $R^7$, $R^8$, $R^9$, and $R^{10}$ of the phosphonium salt of Formula III are independently $C_1$-$C_{12}$ alkyl. In preferred embodiments, the phosphonium salt of Formula III comprises tetrabutylphosphonium chloride.

In the ammonium salt of Formula I, the salt containing a nitrogen heterocycle of Formula II, and the phosphonium salt of Formula III, X is preferably Cl, Br, or OH.

Typically, the pH of a herbicidal mixture containing a salt of Formulas I, II, and/or III and an acidic co-herbicide is from about 4.25 to about 5.5, from about 4.5 to about 5.5, from about 4.75 to about 5.5, from about 5 to about 5.5 or from about 4 to about 5. The pH of the herbicidal mixture may be adjusted by addition of acid or base (e.g., KOH or NaOH) depending upon the desired pH.

Typically, an amount of adjuvant is added to the herbicidal mixture to achieve a molar ratio of auxin herbicide to salt of Formula I, II, and/or III from about 1:3 to about 3:1, or from about 1:2 to about 3:1, or from about 1:1 to about 3:1.

The present invention is also directed to standalone adjuvant compositions comprising a salt selected from the group consisting of (a) an ammonium salt of Formula I, (b) a salt containing a nitrogen heterocycle of Formula II, and (c) a phosphonium salt of Formula III as described herein and one or more surfactants as described herein. In various embodiments, the adjuvant composition is a concentrate composition having a salt concentration greater than about 20 wt. %, about 30 wt. %, about 40 wt. %, about 50 wt. %, or about 60 wt. %.

In accordance with various embodiments of the present invention, the herbicidal mixture may further comprise a surfactant to enhance the herbicidal effectiveness of the auxin herbicide and/or optional co-herbicide. Surfactants are may be included in the herbicidal mixtures to facilitate herbicide retention, uptake and translocation into the plant foliage and thereby enhance herbicidal effectiveness. A weight ratio (a.e.) of total herbicide to surfactant generally ranges from about 1:1 to about 20:1, from about 2:1 to about 10:1, or from about 3:1 to about 8:1.

Some or all of the surfactant of the herbicidal mixture may be supplied from an adjuvant composition described herein. Some or all of the surfactant may also be incorporated from a standalone surfactant composition, auxin herbicide concentrate or dilution thereof, and/or co-herbicide concentrate or dilution thereof (when a co-herbicide is added).

The surfactant may include one or more surfactants known in the art. Known surfactants for use in the present invention include alkoxylated tertiary etheramines, alkoxylated quaternary etheramines, alkoxylated etheramine oxides, alkoxylated tertiary amines, alkoxylated quaternary amines, alkoxylated polyamines, sulfates, sulfonates, phosphate esters, alkylpolysaccharides, alkoxylated alcohols, amidoalkylamines and combinations thereof.

Examples of alkoxylated tertiary etheramine surfactants include, any of the TOMAH E series surfactants, such as TOMAH E-14-2 (bis-(2-hydroxyethyl) isodecyloxypropylamine), TOMAH E-14-5 (poly(5)oxyethylene isodecyloxypropylamine), TOMAH E-17-2, TOMAH E-17-5 (poly(5)oxyethylene isotridecyloxypropyl amine), TOMAH E-19-2, TOMAH E-18-2, TOMAH E-18-5 (poly(5)oxyethylene octadecylamine), TOMAH E-18-15, TOMAH E-19-2 (bis-(2-hydroxyethyl) linear alkyloxypropylamine), TOMAH E-S-2, TOMAH E-S-15, TOMAH E-T-2 (bis-(2-hydroxyethyl) tallow amine), TOMAH E-T-5 (poly(5)oxyethylene tallow amine), and TOMAH E-T-15 (poly(15)

oxyethylene tallow amine), all of which are available from Air Products and Chemicals, Inc. Specific alkoxylated quaternary etheramine surfactants for use in the herbicidal mixture of the present invention include, for example, TOMAH Q-14-2, TOMAH Q-17-2, TOMAH Q-17-5, TOMAH Q-18-2, TOMAH Q-S, TOMAH Q-S-80, TOMAH Q-D-T, TOMAH Q-DT-HG, TOMAH Q-C-15, and TOMAH Q-ST-50, all of which are available from Air Products and Chemicals, Inc.

Examples of alkoxylated etheramine oxide surfactants include any of the TOMAH AO series of surfactants, such as TOMAH AO-14-2, TOMAH AO-728, TOMAH AO-17-7, TOMAH AO-405, and TOMAH AO-455, all of which are available from Air Products and Chemicals, Inc. Alkoxylated tertiary amine oxide surfactants include, for example, any of the AROMOX series of surfactants, including AROMOX C/12, AROMOX C/12W, AROMOX DMC, AROMOX DM16, AROMOX DMHT, and AROMOX T/12 DEG, all of which are available from Akzo Nobel.

Alkoxylated tertiary amine surfactants include, for example, ETHOMEEN T/12, ETHOMEEN T/20, ETHOMEEN T/25, ETHOMEEN T/30, ETHOMEEN T/60, ETHOMEEN C/12, ETHOMEEN C/15, and ETHOMEEN C/25, all of which are available from Akzo Nobel. Alkoxylated quaternary amine surfactants include, for example, ETHOQUAD T/12, ETHOQUAD T/20, ETHOQUAD T/25, ETHOQUAD C/12, ETHOQUAD C/15, and ETHOQUAD C/25, all of which are available from Akzo Nobel.

Alkoxylated polyamine surfactants include, for example, ethoxylates of ADOGEN 560 (N-coco propylene diamine) containing an average of from 2EO to 20EO, for example, 4.8, 10 or 13.4EO; ethoxylates of ADOGEN 570 (N-tallow propylene diamine) containing an average of form 2EO to 20EO, for example, 13EO; and ethoxylates of ADOGEN 670 (N-tallow propylene triamine) containing an average of from 3EO to 20EO, for example, 14.9EO, all of which are available from Witco Corp. Other polyamine surfactants for use in the present invention include Triamine C, Triamine OV, Triamine T, Triamine YT, Triameen Y12D, Triameen Y12D-30, Tetrameen OV, Tetrameen T3, all of which are available from Akzo Nobel.

Sulfate surfactants include, for example, sodium nonylphenol ethoxylate sulfate (4 EO), sodium nonylphenol ethoxylate sulfate (10 EO), WITCOLATE 1247H, WITCOLATE 7093, WITCOLATE 7259, WITCOLATE 1276, WITCOLATE LES-60A, WITCOLATE LES-60C, WITCOLATE 1050, WITCOLATE WAQ, WITCOLATE D-51-51 and WITCOLATE D-51-53, all of which are available from Witco Corp. Sulfonate surfactants include, for example, WITCONATE 93S, WITCONATE NAS-8, WITCONATE AOS, WITCONATE 60T and WITCONATE 605, all of which are available from Witco Corp.

Phosphate esters of alkoxylated alcohol surfactants include, for example, EMPHOS CS-121, EMPHOS PS-400, and WITCONATE D-51-29, available from Witco Corp. Other examples include the PHOSPHOLAN series surfactants available from Akzo Nobel.

Alkylpolysaccharides are yet another suitable class of surfactants. Examples of alkylpolysaccharide surfactants include alkylpolyglucoside (APG) surfactants such as AGNIQUE PG8107-G (AGRIMUL PG 2067) available from BASF. Other representative alkylpolysaccharide surfactants include APG 225, APG 325, APG 425, APG 625, GLUCOPON 600, PLANTAREN 600, PLANTAREN 1200, PLANTAREN 1300, PLANTAREN 2000, AGRIMUL PG 2076, AGRIMUL PG 2067, AGRIMUL PG 2072, AGRIMUL PG 2069, AGRIMUL PG 2062, AGRIMUL PG 2065, and BEROL AG 6202.

Alkoxylated alcohol surfactants include, for example, EMULGIN L, PROCOL LA-15 (from Protameen); BRIJ 35, BRIJ 56, BRIJ 76, BRIJ 78, BRIJ 97, BRIJ 98 (from Sigma Chemical Co.); NEODOL 25-12 and NEODOL 45-13 (from Shell); HETOXOL CA-10, HETOXOL CA-20, HETOXOL CS-9, HETOXOL CS-15, HETOXOL CS-20, HETOXOL CS-25, HETOXOL CS-30, PLURAFAC A38 and PLURAFAC LF700 (from BASF); ST-8303 (from Cognis); AROSURF 66 E10 and AROSURF 66 E20 (from Witco/Crompton); ethoxylated (9.4 EO) tallow, propoxylated (4.4 EO) tallow and alkoxylated (5-16 EO and 2-5 PO) tallow (from Witco/Crompton). Other examples are SURFONIC NP95 and the SURFONIC LF-X series from Huntsman Chemical Co. and the TERGITOL series from Dow.

In some instances, one or more amidoalkylamine surfactants may be included to enhance the stability of the herbicidal mixture. Examples of APA surfactants include ARMEEN APA 2, ARMEEN APA 6, ARMEEN APA 8, ARMEEN APA 10, ARMEEN APA 12, ACAR 7051, ACAR 7059 and ADSEE C80W (Akzo Nobel).

The herbicidal mixture may further comprise other conventional adjuvants or excipients known to those skilled in the art. Hence, the herbicidal mixture may further comprise one or more additional ingredients selected from, without limitation, foam-moderating agents, preservatives or antimicrobials, antifreeze agents, solubility-enhancing agents, dyes, and thickening agents.

As noted, the present invention also provides for a method of preparing the herbicidal mixtures. The method comprises combining an auxin herbicide, an optional co-herbicide and an adjuvant comprising a salt selected from the group consisting of (a) an ammonium salt of Formula I, (b) a salt containing a nitrogen heterocycle of Formula II, (c) a phosphonium salt of Formula III, and mixtures thereof as described herein in a liquid medium such as water. In various embodiments, one or more surfactants are included in the herbicidal mixture. The herbicidal mixtures may be prepared from various concentrates. For example, in some embodiments, the herbicidal mixture is a concentrate composition that is prepared by combining a premix concentrate composition comprising the auxin herbicide and the optional co-herbicide with an adjuvant composition comprising one or more salts of Formulas I, II, and III. An application mixture may be prepared by diluting the concentrate composition comprising the auxin herbicide, optional co-herbicide, and adjuvant with water or other solvent as desired. In other embodiments, a concentrate composition may be prepared by combining an auxin herbicide concentrate and one or more optional co-herbicide concentrates with the adjuvant composition. Optional surfactant may be present in any premix concentrate, auxin herbicide concentrate, co-herbicide concentrate, adjuvant composition, or standalone composition. Any of the abovementioned concentrates may be diluted with water or other solvent before, during, or after the preparation process.

The present invention is effective in reducing auxin herbicide volatility. As such, the present invention provides a method of reducing off-site movement of an auxin herbicide following application of the herbicidal mixture. The method comprises combining an auxin herbicide and an adjuvant comprising one or more salts of Formulas I, II, and III as previously described. The method further includes applying the herbicidal mixture to the foliage of the auxin-susceptible plants.

In accordance with methods of use of the present invention, the herbicidal mixture may be applied to the foliage of unwanted plants as a spray application mixture by methods known in the art. The application mixture is applied to the foliage of a plant or plants at an application rate sufficient to give a commercially acceptable rate of weed control. Depending on plant species and growing conditions, the period of time required to achieve a commercially acceptable rate of weed control can be as short as a week or as long as three weeks, four weeks or 30 days. The application rate is usually expressed as amount of herbicide per unit area treated, e.g., grams acid equivalent per hectare (g a.e./ha) and can readily be determined by those skilled in the art.

The compositions and methods of the present invention are particularly suited for application to transgenic plants having certain herbicide tolerance traits. For example, an application mixture of the present invention comprising an auxin herbicide comprising dicamba salt or 2,4-D salt would be especially suited for applying to the foliage of auxin-susceptible plants growing in and/or adjacent to a field of crop plants comprising transgenic crop plants having a dicamba tolerance trait or 2,4-D tolerance trait, respectively. Further, an application mixture of the present invention comprising an auxin herbicide and a co-herbicide comprising glyphosate or glufosinate (or salts thereof) would be especially suited for applying to the foliage of auxin-susceptible plants and plants susceptible to the co-herbicide growing in and/or adjacent to a field of crop plants comprising transgenic crop plants having stacked auxin tolerance trait and a glyphosate or glufosinate tolerance trait, respectively.

The application mixture of the present invention can be applied pre-planting of the crop plant, such as from about 2 to about 3 weeks before planting auxin-susceptible crop plants or crop plants not having an auxin tolerance trait. Crop plants that are not susceptible to auxin herbicides, such as corn, or plants having auxin tolerance and co-herbicide tolerance traits typically have no pre-planting restriction. The application mixture can be applied immediately before planting such crops, at planting, or post-emergence to such crop plants to control auxin-susceptible weeds and co-herbicide-susceptible weeds in a field of the crop plants.

EXAMPLES

The following non-limiting examples are provided to further illustrate the present invention.

Example 1

In this example, various herbicidal mixtures were prepared in accordance with the present invention. In general, the herbicidal mixtures contain the diglycolamine dicamba salt (CLARITY), a glyphosate salt co-herbicide, an adjuvant comprising a salt of Formulas I, II, or III, and water as needed. Table 1 lists the components of each herbicidal mixture.

A pH measurement is also provided for each herbicidal mixture. The pH measurements were obtained by immersing the probe of a calibrated pH meter into each mixture and recording the digital reading. The pH measurements were made using a Mettler Toledo model SevenEasy pH meter with a Thermo Scientific ROSS Sure-flow pH probe. The pH meter was calibrated in accordance with the manufacturer's recommended protocol at pH 4 and pH 7 using standard buffer solutions.

Volatility tests (tube tests and humidome tests) were conducted to measure the effect of the adjuvant salts on dicamba concentration in air. The protocols for the tube tests and humidome tests are described below.

Tube Test Protocol

To measure the dicamba concentration in the gas phase (air) volatilized from the spray solutions via a tube test, 10 mL samples of each solution were placed into a 50 mL plastic centrifuge tube with one hole approximately ⅛ in (3.2 mm) diameter drilled into the tube at the mark between 20 mL and 30 mL lines. A 22 mm×30 mm Polyurethane Foam (PUF) filter, cut from a 76 mm length, available from SKC Inc., catalog # P22692, was placed into a glass tube of approximately 20 mm diameter with parafilm wrapped around the outside to obtain a snug fit into the top of the centrifuge tube. A hose was connected to the other end of the glass tube leading to a vacuum line. The air flow was regulated to approximately 2 L/min using a flow controller. Air was pulled through the tube at approximately 2 L/min for 24 hours. Note that the air conditions of flow rate, temperature, pressure and composition (e.g., relative humidity) are not narrowly critical as long as the various samples are analyzed under similar conditions. For instance, air at from about 5° C. to about 40° C., from about 0.5 to about 1.5 bar pressure, from about 0% to about 95% relative humidity, and at a flow rate of from about 0.1 to 10 L/min-mL sample could be suitably used for volatility analysis. In this test, the air pulled through the tubes was at about 35° C. and about 40% relative humidity. The PUF filter was removed from the glass tube, extracted with 20 mL methanol and the resulting solution analyzed for dicamba concentration using liquid chromatography-mass spectroscopy (LC-MS) methods known in the art.

Humidome Test Protocol

Humidomes (24.25 L) were obtained from Hummert International (Part Nos. 14-3850-2 for humidomes and 11-3050-1 for 1020 flat tray) and modified by cutting a 2.2 cm diameter hole on one end approximately 5 cm from the top to allow for insertion of a glass air sampling tube (22 mm OD) containing a PUF filter cut to 30 mm in length. The sampling tube was secured with a VITON o-ring on each side of the humidome wall. The air sampling tube external to the humidome was fitted with tubing that was connected to a vacuum manifold immediately prior to sampling.

The flat tray beneath each humidome was filled with 1 liter of sifted dry or wet 50/50 soil (50% Redi-Earth and 50% US 10 Field Soil) to a depth of about 1 cm. The herbicidal mixtures were sprayed on to the soil of each humidome at an application rate of 1.0 lb/acre a.e. at 10 gallons per acre. The flat tray bottom containing the dicamba formulation on soil was covered with a humidome lid, and the lid was secured with clamps. The assembled humidomes were placed in a temperature and humidity controlled environment and connected to a vacuum manifold through the air sampling line. The humidome chambers were set at 35° C. and 40% RH. Air was drawn through the humidomes and PUF filter at a rate of 2 liters per minutes (LPM) for 24 hours at which point the air sampling was stopped. The humidomes were then removed from the controlled environment and the PUF filter was removed. The PUF filter was extracted with 20 mL of methanol and the solution was analyzed for dicamba using LC-MS methods known in the art. Four separate humidomes were sprayed with the same herbicidal mixture to obtain four replicate measurements for each herbicidal mixture.

The results of the volatility tests are presented in Table 1. The reduction in volatility is calculated relative to the volatility of the control samples containing the diglycolamine salt of dicamba (CLARITY) and the glyphosate salt specified. The results indicate that the adjuvant salts are effective in significantly reducing dicamba volatility and/or counteracting the negative impact on the volatility of the auxin herbicide due to the presence of a glyphosate salt co-herbicide.

TABLE 1

| Herbicidal Mixture No. | DGA Dicamba (wt. % a.e.) | Co-herbicide | Co-herbicide (wt. % a.e.) | Salt Adjuvant | Molar ratio dicamba:Salt Adjuvant | pH | Volatility Reduction compared to Control (%) | Volatility Test Type |
|---|---|---|---|---|---|---|---|---|
| Control-A | 2.0 | potassium glyphosate | 6.0 | — | — | 4.08 | — | Tube |
| 3-1 | 2.0 | potassium glyphosate | 6.0 | tetraethylammonium chloride | 1:1 | 4.07 | 42 | Tube |
| 3-2 | 2.0 | potassium glyphosate | 6.0 | tetraethylammonium chloride | 1:2 | 4.07 | 60 | Tube |
| 3-3 | 2.0 | potassium glyphosate | 6.0 | 1-butyl-1-methylpyrrolidinium chloride | 1:1 | 4.08 | 60 | Tube |
| 3-4 | 2.0 | potassium glyphosate | 6.0 | 1-ethyl-3-methylimidazolium chloride | 1:1 | 4.05 | 60 | Tube |
| 3-5 | 2.0 | potassium glyphosate | 6.0 | 1-butyl-3-methylimidazolium chloride | 1:1 | 4.06 | 60 | Tube |
| 3-6 | 2.0 | potassium glyphosate | 6.0 | 1-methyl-3-octylimidazolium chloride | 1:1 | 4.12 | 80 | Tube |
| Control-B | 2.0 | potassium glyphosate (POWERMAX) | 6.0 | — | — | 4.37 | — | Tube |
| 3-7 | 2.0 | potassium glyphosate (POWERMAX) | 6.0 | tributylmethylammonium chloride | 1:1 | 4.36 | 74 | Tube |
| 3-8 | 2.0 | potassium glyphosate (POWERMAX) | 6.0 | tetrabutylammonium chloride | 1:1 | 4.38 | 89 | Tube |
| 3-9 | 2.0 | potassium glyphosate (POWERMAX) | 6.0 | tetrabutylammonium chloride | 1:0.33 | 4.32 | 70 | Tube |
| 3-10 | 2.0 | potassium glyphosate (POWERMAX) | 6.0 | tetrabutylphosphonium chloride | 1:1 | 4.37 | 87 | Tube |
| Control-C | 0.5 | potassium glyphosate | 1.5 | — | — | 4.11 | — | Humidome |
| 3-11 | 0.5 | potassium glyphosate | 1.5 | tetrabutylammonium chloride | 1:1 | 4.31 | 85 | Humidome |
| 3-12 | 0.5 | potassium glyphosate | 1.5 | dodecyltrimethylammonium chloride | 1:0.33 | 4.17 | 65 | Humidome |
| 3-13 | 0.5 | potassium glyphosate | 1.5 | cetylpyridinium chloride | 1:1 | 4.17 | 65 | Humidome |
| 3-14 | 0.5 | potassium glyphosate | 1.5 | tetrabutylphosphonium chloride | 1:1 | 4.05 | 85 | Humidome |
| 3-15 | 0.5 | potassium glyphosate | 1.5 | 1-ethyl-3-methylimidazolium chloride | 1:1 | 4.06 | 43 | Humidome |
| 3-16 | 0.5 | potassium glyphosate | 1.5 | cetylpyridinium bromide | 1:1 | 4.17 | 65 | Humidome |
| Control-D | 1.2 | potassium glyphosate (WEATHERMAX) | 2.4 | — | — | 4.6 | — | Humidome |
| 3-17 | 1.2 | potassium glyphosate (WEATHERMAX) | 2.4 | benzalkonium chloride | 1:0.33 | 4.6 | 75 | Humidome |
| 3-18 | 1.2 | potassium glyphosate (WEATHERMAX) | 2.4 | benzalkonium chloride | 1:1 | 4.6 | 92 | Humidome |
| 3-19 | 2.0 | potassium glyphosate | 6.0 | tetraethylammonium chloride | 1:1 | 4.08 | 40 | Humidome |
| 3-20 | 2.0 | potassium glyphosate | 6.0 | tetraethylammonium chloride | 1.2:1 | 4.09 | 47 | Humidome |
| 3-21 | 2.0 | potassium glyphosate | 6.0 | tetraethylammonium chloride | 1.9:1 | 4.07 | 60 | Humidome |
| 3-22 | 2.0 | potassium glyphosate | 6.0 | tetraethylammonium chloride | 2.6:1 | 4.06 | 66 | Humidome |
| Control-E | 1.2 | potassium glyphosate | 2.4 | — | — | 4.11 | — | Humidome |
| 3-23 | 1.2 | potassium glyphosate | 2.4 | 1-ethyl-3-methylimidazolium chloride | 1:1 | 4.11 | 43 | Humidome |
| 3-24 | 1.2 | potassium glyphosate | 2.4 | 1-ethyl-3-methylimidazolium chloride | 1:1 | 4.48 | 80 | Humidome |

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above compositions and processes without departing from the scope of the invention, it is intended that all matter contained in the above description shall be interpreted as illustrative and not in a limiting sense.

What is claimed is:

1. A method of preparing a herbicidal mixture, the method comprising:
   combining an auxin herbicide comprising a first cation and an adjuvant comprising a salt comprising a second cation, wherein the salt is selected from the group consisting of:
   (a) an ammonium salt of Formula I

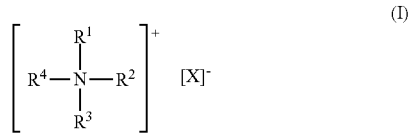

wherein $R^1$, $R^2$, $R^3$, and $R^4$ are each butyl and X is an agronomically acceptable anion;
   (b) a salt containing a nitrogen heterocycle of Formula II

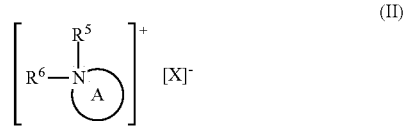

wherein A is a 5 or 6-membered heterocyclic ring; $R^5$ is a $C_1$-$C_{20}$ alkyl; $R^6$ is hydrogen or a $C_1$-$C_6$ alkyl, and X is an agronomically acceptable anion;
   (c) a phosphonium salt of Formula III

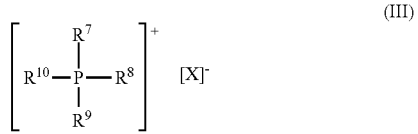

wherein $R^7$, $R^8$, $R^9$, and $R^{10}$ are independently a $C_1$-$C_{12}$ hydrocarbyl and X is an agronomically acceptable anion; and mixtures thereof, and wherein the herbicidal mixture has a total herbicide concentration no greater than about 40% by weight acid equivalent (a.e).

2. A herbicidal mixture, comprising:
   an auxin herbicide comprising a first cation and an adjuvant comprising a salt comprising a second cation, wherein the salt is selected from the group consisting of:
   (a) an ammonium salt of Formula I

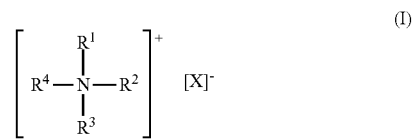

wherein $R^1$, $R^2$, $R^3$, and $R^4$ are each butyl and X is an agronomically acceptable anion;
   (b) a salt containing a nitrogen heterocycle of Formula II

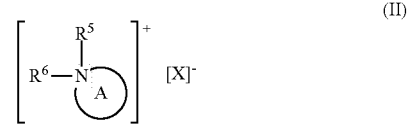

wherein A is a 5 or 6-membered heterocyclic ring; $R^5$ is a $C_1$-$C_{20}$ alkyl; $R^6$ is hydrogen or a $C_1$-$C_6$ alkyl, and X is an agronomically acceptable anion;
   (c) a phosphonium salt of Formula III

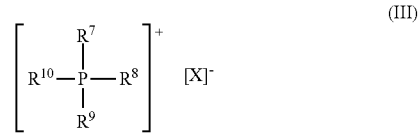

wherein $R^7$, $R^8$, $R^9$, and $R^{10}$ are independently a $C_1$-$C_{12}$ hydrocarbyl and X is an agronomically acceptable anion; and mixtures thereof, and wherein the herbicidal mixture has a total herbicide concentration no greater than about 40% by weight acid equivalent (a.e).

3. The herbicidal mixture of claim 2 wherein the adjuvant comprises an ammonium salt of Formula I

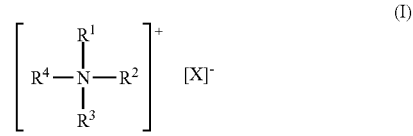

wherein $R^1$, $R^2$, $R^3$, and $R^4$ are each butyl and X is an agronomically acceptable anion.

4. The herbicidal mixture of claim 3 wherein X is Cl.
5. The herbicidal mixture of claim 3 wherein X is Br.
6. The herbicidal mixture of claim 3 wherein X is OH.
7. The herbicidal mixture of claim 2 wherein the molar ratio of auxin herbicide to salt of Formula I is from about 1:1 to about 3:1.
8. The herbicidal mixture of claim 2 wherein the adjuvant comprises a salt containing a nitrogen heterocycle of Formula II

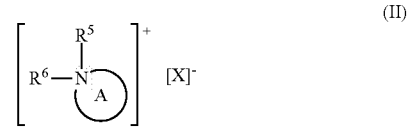

wherein A is a 5 or 6-membered heterocyclic ring; $R^5$ is a $C_1$-$C_{20}$ alkyl; $R^6$ is hydrogen or a $C_1$-$C_6$ alkyl, and X is an agronomically acceptable anion.

9. The herbicidal mixture of claim 8 wherein A is a substituted imidazole ring, a substituted pyridine ring, or a substituted pyrrolidine ring;

$R^5$ is $C_1$-$C_{12}$ alkyl; and/or the salt of Formula II is selected from the group consisting of 1-butyl-1-methyl-pyrrolidinium chloride, 1-ethyl-3-methylimidazolium chloride, 1-butyl-3-methylimidazolium chloride, 1-methyl-3-octylimidazolium chloride, cetylpyridinium chloride, and cetylpyridinium bromide.

10. The herbicidal mixture of claim 3 wherein the salt of Formula I is selected from the group consisting of tetrabutylammonium chloride and tetrabutylammonium bromide.

11. The herbicidal mixture of claim 2 wherein the adjuvant comprises a phosphonium salt of Formula III

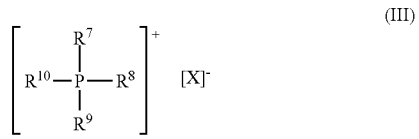

wherein $R^7$, $R^8$, $R^9$, and $R^{10}$ are independently a $C_1$-$C_{12}$ hydrocarbyl and X is an agronomically acceptable anion.

12. The herbicidal mixture of claim 11 wherein $R^7$, $R^8$, $R^9$, and $R^{10}$ are independently $C_1$-$C_{12}$ alkyl; and/or the salt of Formula III comprises tetrabutylphosphonium chloride.

13. The herbicidal mixture of claim 2 wherein X is Cl, Br, or OH.

14. The herbicidal mixture of claim 2 wherein the auxin herbicide is selected from the group consisting of 3,6-dichloro-2-methoxybenzoic acid (dicamba); 2,4-dichlorophenoxyacetic (2,4-D); 4-(2,4-dichlorophenoxy)butanoic acid (2,4-DB); 2-(2,4-dichlorophenoxy)propanoic acid (dichloroprop); 2-(4-chloro-2-methylphenoxy)acetic acid (MCPA); 4-(4-chloro-2-methylphenoxy)butanoic acid (MCPB); 4-amino-3,6-dichloro-2-pyridinecarboxylic acid (aminopyralid); 3,6-dichloro-2-pyridinecarboxylic acid (clopyralid); 2-[(4-amino-3,5-dichloro-6-fluoro-2-pyridinyl)oxy]acetic acid (fluroxypyr); [(3,5,6-trichloro-2-pyridinyl)oxy]acetic acid (triclopyr); 2-(4-chloro-2-methylphenoxy)propanoic acid (mecoprop); 4-amino-3,5,6-trichloro-2-pyridinecarboxylic acid (picloram); 3,7-dichloro-8-quinolinecarboxylic acid (quinclorac); 6-amino-5-chloro-2-cyclopropyl-4-pyrimidinecarboxylic acid (aminocyclopyrachlor); agriculturally acceptable salts or other derivatives of any of these herbicides; racemic mixtures and resolved isomers thereof; and mixtures thereof.

15. The herbicidal mixture of claim 2 wherein the auxin herbicide comprises a salt of dicamba selected from the group consisting of the monoethanolamine salt, diethanolamine salt, isopropylamine, diglycolamine salt, potassium salt, sodium salt dimethylamine salt and mixtures thereof.

16. The herbicidal mixture of claim 2 wherein the auxin herbicide comprises a salt of 2,4-D.

17. The herbicidal mixture of claim 2 wherein the herbicidal mixture further comprises a co-herbicide selected from the group consisting of N-(phosphonomethyl)glycine (glyphosate); DL-phosphinothricin (glufosinate); atrazine, acetochlor, fomesafen, flumioxazin, lactofen, sulfentrazone, metribuzin, clethodim, sethoxydim, metolachlor, alachlor, fenoxaprop, fluazifop, haloxyfop-methyl, paraquat, trialkoxydim; and salts and combinations thereof.

18. The herbicidal mixture of claim 17 wherein the co-herbicide comprises a salt of glyphosate.

19. The herbicidal mixture of claim 2 wherein the pH of the herbicidal mixture is from about 4 to about 5.5.

20. The herbicidal mixture of claim 2 wherein the herbicidal mixture further comprises a surfactant selected from the group consisting of alkoxylated tertiary etheramines, alkoxylated quaternary etheramines, alkoxylated etheramine oxides, alkoxylated tertiary amines, alkoxylated quaternary amines, alkoxylated polyamines, sulfates, sulfonates, phosphate esters, alkyl polysaccharides, alkoxylated alcohols, amidoalkylamines and combinations thereof.

21. The herbicidal mixture of claim 2 wherein the herbicidal mixture is a concentrate composition wherein the total herbicide content is from about 10 wt. % a.e. to about 40 wt. % a.e.

22. The herbicidal mixture of claim 2 wherein the herbicidal mixture is an application mixture wherein the total herbicide content is from about 0.1 wt. % a.e. to about 10 wt. % a.e.

23. The herbicidal mixture of claim 22 wherein the herbicidal mixture further comprises a co-herbicide and the concentration of the co-herbicide in the application mixture is from about 0.5 wt. % a.e. to about 8 wt. % a.e.

24. The herbicidal mixture of 22 wherein the concentration of the auxin herbicide in the herbicidal mixture is from about 0.25 wt. % (a.e.) to about 4 wt. % (a.e.).

25. The herbicidal mixture of claim 2 wherein the concentration of the adjuvant in the herbicidal mixture is from about 0.1 wt. % to about 10.0 wt. %.

26. The herbicidal mixture of claim 2 wherein the molar ratio of auxin herbicide to salt of Formula I, II, and/or III is from about 1:1 to about 3:1.

27. The method of claim 1 wherein the molar ratio of auxin herbicide to salt of Formula I, II, and/or III is from about 1:1 to about 3:1.

* * * * *